(12) United States Patent
Meng et al.

(10) Patent No.: US 7,126,034 B2
(45) Date of Patent: Oct. 24, 2006

(54) PROCESS FOR PREPARATION OF 1,3-PROPANEDIOL

(75) Inventors: Xiangsheng Meng, Chanhassen, MN (US); Timothy W. Abraham, Minnetonka, MN (US); Paraskevas Tsobanakis, Inver Grove Heights, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 10/532,938

(22) PCT Filed: Oct. 30, 2003

(86) PCT No.: PCT/US03/34470

§ 371 (c)(1),
(2), (4) Date: Apr. 28, 2005

(87) PCT Pub. No.: WO2004/041421

PCT Pub. Date: May 21, 2004

(65) Prior Publication Data

US 2005/0283029 A1    Dec. 22, 2005

(51) Int. Cl.
| | | |
|---|---|---|
| C07C 29/136 | (2006.01) | |
| C07C 29/14 | (2006.01) | |
| C07C 29/141 | (2006.01) | |
| C07C 29/143 | (2006.01) | |
| C07C 29/147 | (2006.01) | |
| C07C 29/149 | (2006.01) | |

(52) U.S. Cl. ..................................... 568/885
(58) Field of Classification Search ................ 568/885
See application file for complete search history.

(56) References Cited

U.S. PATENT DOCUMENTS

| | | |
|---|---|---|
| 2,094,611 A | 10/1937 | Lazier |
| 3,770,837 A | 11/1973 | Favstritsky et al. |
| 4,326,072 A | 4/1982 | Kruse et al. |
| 4,611,085 A | 9/1986 | Kitson |
| 5,061,671 A | 10/1991 | Kitson et al. |
| 5,066,815 A | 11/1991 | Sayo et al. |
| 5,387,753 A | 2/1995 | Scarlett et al. |
| 5,395,991 A | 3/1995 | Scarlett et al. |
| 5,426,246 A | 6/1995 | Nagahara et al. |
| 5,698,749 A | 12/1997 | Pedersen et al. |
| 5,786,524 A | 7/1998 | Powell et al. |
| 5,981,769 A | 11/1999 | Baur et al. |
| 6,191,321 B1 | 2/2001 | Forschner et al. |
| 6,288,266 B1 | 9/2001 | Moore et al. |
| 6,355,848 B1 | 3/2002 | Antons et al. |
| 6,376,414 B1 | 4/2002 | Antons et al. |
| 6,403,844 B1 | 6/2002 | Zhang et al. |
| 6,617,478 B1 | 9/2003 | Lee et al. |
| 2002/0087035 A1 | 7/2002 | Cortright et al. |
| 2002/0087036 A1* | 7/2002 | Haas et al. .................. 568/885 |

FOREIGN PATENT DOCUMENTS

| | | |
|---|---|---|
| GB | 2 362 157 A | 3/2000 |
| JP | 10015388 A2 | 1/1998 |
| JP | 11012207 A2 | 1/1999 |
| JP | 2001002603 A2 | 1/2001 |
| JP | 2001002604 A2 | 1/2001 |
| JP | 2001002605 A2 | 1/2001 |

* cited by examiner

*Primary Examiner*—Elvis O. Price
(74) *Attorney, Agent, or Firm*—Fish & Richardson P.C.

(57) ABSTRACT

Disclosed is a process for hydrogenating 3-hydroxypropionic acid, or esters thereof, or mixtures of the acid and the ester, in a liquid phase, in the presence of a ruthenium catalyst, alone, or in combination with at least one or more additional metal catalyst wherein the metal is molybdenum, tungsten, titanium, zirconium, niobium, vanadium, chromium, or mixtures of the metals.

22 Claims, No Drawings

PROCESS FOR PREPARATION OF 1,3-PROPANEDIOL

FIELD OF THE INVENTION

This invention relates to a process for preparing 1,3-propanediol from 3-hydroxypropionic acid or derivatives thereof.

BACKGROUND OF THE INVENTION

Various methods for producing 1,3-propanediol are known. Included within such methods is the production of 1,3-propanediol by the catalytic hydrogenation of methyl 3-hydroxypropionate in the presence of a copper zinc oxide catalyst, as shown in U.S. Pat. No. 6,191,321. It is also known from U.S. Pat. No. 3,770,837 that 1,3-propanediol may be prepared by hydrogenating beta-hydroxypropionic acid or beta-propiolactone in the presence of rhenium black catalyst. Furthermore, it is described in U.S. Pat. No. 6,025,184, that 1,3-propanediol may be produced from glucose by a fermentation procedure.

SUMMARY OF THE INVENTION

It is accordingly an object of the present invention to provide a new process for preparing 1,3-propanediol.

It is a further object of this invention to provide a new process for preparing 1,3-propanediol in good yield.

These and other objects and advantages of the present invention will be apparent to those skilled in the art from the following detailed description and claims.

In accordance with the present invention, it has been found that the above and still further objects are achieved by hydrogenating 3-hydroxypropionic acid, or esters of the acid or mixtures, in the presence of a specific catalyst, in a liquid phase, to prepare 1,3-propanediol. The catalysts that are used in the process of the present invention are ruthenium metal, or compounds of ruthenium, supported or unsupported, alone or in combination with at least one or more additional metal(s) selected from molybdenum, tungsten, titanium, zirconium, niobium, vanadium or chromium, or compound of the additional metal(s).

The 1,3-propanediol product is a known compound having many applications, and the products produced herein are useful in such applications.

Another object of the invention is to provide a process that includes using 3-hydroxypropionic acid that has been produced via a fermentation process that can utilize genetically engineered organisms, such as bacteria, yeast, or fungi. The biologically produced 3-hydroxypropionic acid generally is in the form of a salt, such as an ammonium salt, in the resulting fermentation both. To separate the ammonium salt and form the free acid an organic extractant is added to the reactor, followed by heating.

DETAILED DESCRIPTION OF THE INVENTION

The process of the present invention relates to the preparation of 1,3-propanediol, by hydrogenating 3-hydroxypropionic acid, or esters of the acid or mixtures of the acid and ester, in the presence of a specific catalyst, in a liquid phase.

The present invention provides a process for producing 1,3-propanediol from 3-hydroxypropionic acid or esters of 3-hydroxypropionic acid having the formula, $HOCH_2 CH_2 CO_2R$, wherein R is a $C_1$-$C_{20}$ alkyl group, linear or branched, optionally substituted by halogen, alkoxy, amino, alkylamino, or hydroxyl groups, or a $C_1$-$C_{20}$ aryl group, linear or branched, optionally substituted by halogen, alkoxy, amino, alkylamino, or hydroxyl groups. Exemplary of the esters of 3-hydroxypropionic acid suitable for use herein are $C_1$-$C_5$ esters of 3-hydroxypropionic acid.

The catalysts that are used in the process of the present invention are ruthenium metal or compounds of ruthenium, either supported or unsupported, alone, or in combination with at least one or more additional metal(s) selected from molybdenium, tungsten, titanium, zirconium, niobium, vanadium or chromium, or a compound of the additional metal(s).

The compounds of both the ruthenium metal, and the additional metal(s), include oxides, hydroxides, halides, nitrates, carboxylates and the like. Indeed, any compound of the ruthenium and the additional metal is suitable for use herein provided that the hydrogenation of the 3-hydroxypropionic acid, in liquid phase, to prepare 1,3-propanediol, may be successfully achieved.

The ruthenium metal or compound thereof, and/or the additional metal(s), or compound thereof, may be utilized in supported or unsupported form. If utilized in supported form, the method of preparing the supported catalyst is not critical and can be any technique such as impregnation of the support or deposition on the support.

These techniques are well known and require no description. The metal in the supported catalyst comprises up to about 50% by weight of the catalyst, particularly up to about 20% by weight of the catalyst.

Any suitable support may be utilized provided that the preparation of 1,3-propanediol by the present process may be achieved. Supports that may be used herein include, but are not limited to, alumina, titania, silica, zirconia, carbons, carbon blacks, graphites, silicates, zeolites, aluminosilicate zeolites, aluminosilicate clays, and the like.

When two or more catalysts are used they are added as distinct compounds that are not in the form of an adduct or reaction product. The catalysts however, can be pre-mixed and added simultaneously. The catalyst concentration used in the present process ranges, from about 0.01 to about 100% by weight of ruthenium, based on the weight of 3-hydroxypropionic acid reactant. When an additional metal catalyst is used in combination with the ruthenium catalyst, the amount of the additional metal catalyst utilized ranges preferably, from about 1 to about 100% by weight, based on the weight of the 3-hydroxypropionic acid reactant.

The hydrogenation process of the present invention is carried out in liquid phase. The liquid phase includes water, organic solvents that are not hydrogenatable, such as any aliphatic or aromatic hydrocarbon, alcohols, ethers, toluene, decalin, dioxane, diglyme, n-heptane, hexane, xylene, benzene, tetrahydrofuran, cyclohexane, methylcyclohexane, and the like, and mixtures of water and organic solvent(s).

The hydrogenation process of the present invention may be carried out batch wise, semi-continuously, or continuously.

The present process may be carried out in any suitable apparatus. Exemplary of such apparatus are stirred tank reactors, trickle-bed reactors, high pressure hydrogenation reactors, and the like.

The hydrogen containing gas utilized in the present process is, typically, commercially pure hydrogen. However, it is not essential that the hydrogen containing gas be commercially pure. The hydrogen containing gas is usable if nitrogen, gaseous hydrocarbons, or oxides of carbon, and similar materials, are present in the hydrogen containing gas.

The hydrogenation process of the present invention is generally carried out at a temperature ranging from about 20° to about 250° C., more particularly from about 100° to about 200° C. Further, the hydrogenation process of the present invention is generally carried out in a pressure range of from about 20 p.s.i. to about 4000 p.s.i. (pounds per square inch), and more particularly, in a pressure range of from about 500 p.s.i. to about 2000 p.s.i. There is no specific residence time required for the present hydrogenation reaction, other than the residence time be adequate to allow the intended product to be produced. More particularly, the residence time for the present hydrogenation ranges from about 1 to about 10 hours.

It has been noted that carrying out the present hydrogenation process may result in the production of reaction by-products, such as n-propanol, acrylic acid and others. Recovery of the reaction by-products that are valuable, is achieved by any method conventional in the art.

The invention will be more readily understood by reference to the following examples. There are, of course, many other forms of this invention which will become obvious to one skilled in the art, once the invention has been fully disclosed, and it will accordingly be recognized that these examples are given for the purpose of illustration only, and are not to be construed as limiting the scope of this invention in any way.

EXAMPLES

In the following examples, the products produced by the hydrogenation processes were analyzed using a Waters 1525 Binary BPLC pump, equipped with a Waters 717 plus Autosampler, and Waters 2410 Refractive Index and Waters 2487 Dual Lambda Absorbance detectors, having a Bio-Rad HP87-H column, 0.004 N sulfuric acid as the mobile phase, a flow rate of 0.6 ml/min, and a column temperature of 60° C.

C./min increase to a final temperature of 200° C. The sample was maintained at 200° C. for about 12.5 minutes prior to injection. Retention times for 1,3 propandion were about 6.8 minutes and about 15.8 minutes for 3-hydroxypropionic acid.

Examples 1–22

Examples 1–22 of the present invention were carried out in the following manner. A catalytic hydrogenation of a solution of 20% 3-hydroxypropionic acid (herein 3-HP) in water was carried out in a stirred autoclave bench top reactor. In the examples, the autoclave reactor was a Parr reactor, available from Parr Instrument Company, Moline, Ill. The concentrations of reactants and resultant products were analyzed by HPLC and, GC. An aqueous solution of the 3-hydroxypropionic acid (3-BP) in water, the liquid phase, and the catalyst were charged into the autoclave reactor. The reactor was flushed three times with hydrogen. The reactor was then pressurized to about 200 p.s.i. of hydrogen. The reactor was heated to the desired temperature, and, then, pressurized to the desired hydrogen pressure. The mixture of reactants was stirred, at the desired temperature and hydrogen pressure, in the autoclave reactor for a desired period of time. Thereafter, the autoclave reactor was cooled to room temperature, and the hydrogen pressure was released. The resultant reaction mixture was separated by centrifugation and filtration, and the obtained aqueous solution was analyzed by HPLC and GC techniques, to determine the concentrations of the reactants and the products that were prepared. The processing conditions, and the product data are reported for the examples in the Table 1, wherein a ruthenium catalyst is solely utilized, and in Table 2, wherein the catalyst used is a combination of a ruthenium catalyst and an additional metal-containing catalyst.

TABLE 1

Preparation of 1,3-propanediol (1,3-PDO) by Hydrogenating 3-hydroxypropionic Acid (3-HP)

| Example | 20% 3-HP in water, g | Liquid Phase, g | Catalyst, g | Temp. ° C. | Pressure p.s.i. | Reaction Time, Hours | 1,3-PDO yield, % |
|---|---|---|---|---|---|---|---|
| 1 | 10 | None | 3.25 g Ru/C[2] | 100 | 1500 | 16 | 47 |
| 2 | 10 | 40 g A[1] | 3.20 g Ru/C[2] | 100 | 1500 | 16 | 41 |
| 3 | 21 | 33 g A[1] | 6.28 g Ru/C[2] | 100 | 1500 | 20 | 34 |
| 4 | 11 | 40 g A[1] | 6.63 g Ru/C[2] | 80 | 2100 | 20 | 31 |
| 5 | 11 | 42 g xylene | 6.79 g Ru/C[2] | 80 | 2100 | 20 | 26 |
| 6 | 10 | 41 g heptane | 6.48 g Ru/C[2] | 80 | 2100 | 20 | 36 |

[1]A is ISOPAR K $C_{10}$–$C_{11}$ paraffin available from Exxon Mobil Company
[2]Ru/C is about 5% ruthenium metal on carbon having about 50% water. This product is available Description of GC Paragraph, and Description of PMC Material The 3-hydroxypropionic acid was purchased as a 30% solution from TCl, Oregon. This product, however, contains approximately 20% monomer and the remaining 10% of the 3-hydroxypropionic acid content is in the form of various dimers.

The protocol for the gas chromatograph was as follows: A J & W DB-Waxetr 30 m×32 mm 0.5 um film column was used with an internal oven temperature at 90° C. with a 20°

TABLE 2

Preparation of 1,3-Propanediol (1,3-PDO) by Hydrogenating 3-hydroxypropionic Acid (3-HP)

| Example | 20% 3-HP in water, g | Liquid Phase, g | Catalyst, g | Temp ° C. |
|---|---|---|---|---|
| 7 | 21 | 30 g water | 3.27 g Ru/C[2] and 1.24 g MoO$_2$ | 150 |

TABLE 2-continued

Preparation of 1,3-Propanediol (1,3-PDO) by
Hydrogenating 3-hydroxypropionic Acid (3-HP)

| | | | | |
|---|---|---|---|---|
| 8 | 10 | 41 g A[1] | 1.64 g Ru/C[2] and 0.63 g $MoO_2$ | 150 |
| 9 | 21 | 30 g A[1] | 6.59 g Ru/C[2] and 0.35 g $MoO_3$ | 100 |
| 10 | 20 | 31 g A[1] | 6.47 g Ru/C[2] and 0.35 g $MoO_3$ | 80 |
| 11 | 10 | 40 g A[1] | 1.69 g Ru/C[2] and 0.31 g $MoO_3$ | 100 |
| 12 | 11 | 41 g A[1] | 3.39 g Ru/C[2] and 0.32 g $MoO_3$ | 100 |
| 13 | 10 | 40 g A[1] | 3.23 g Ru/C[2] and 0.61 g $MoO_3$ | 120 |
| 14 | 11 | 47 g A[1] | 3.5 g Ru/C[2] and 0.67 g $MoO_2$ | 120 |
| 15 | 10* | 40 g A[1] | 1.75 g Ru/C[2] and 0.66 g $MoO_2$ | 150 |
| 16 | 10 | 41 g A[1] | 1.63 g Ru/C[2] and 0.61 g Mo | 150 |
| 17 | 10 | 40 g A[1] | 1.62 g Ru/C[2] and 0.62 g $MoO_2$ | 135 |
| 18 | 11 | 46 g A[1] | 3.59 g Ru/C[2] and 0.68 g $WO_3$ | 120 |
| 19 | 11 | 40 g A[1] | 3.46 g Ru/C[2] and 0.66 g $ZnO_2$ | 100 |
| 20 | 10 | 41 g A[1] | 3.28 g Ru/C[2] and 0.32 g $TiO_2$ | 100 |
| 21 | 11 | 41 g A[1] | 1.63 g Ru/$Al_2O_3$ and 0.33 g $MoO_2$ | 100 |
| 22 | 10 | 40 g A[1] | 1.7 g Ru/C[2] and 0.61 g $NbO_2$ | 150 |

| Example | Pressure p.s.i. | Reaction Time Hours | 1,3-PDO yield, % |
|---|---|---|---|
| 7 | 1500 | 3 | 60 |
| 8 | 1500 | 3 | 56 |
| 9 | 1500 | 20 | 60 |
| 10 | 1500 | 20 | 37 |
| 11 | 1500 | 20 | 49 |
| 12 | 1500 | 20 | 66 |
| 13 | 1500 | 3 | 42 |
| 14 | 1500 | 3 | 48 |
| 15 | 1500 | 3 | 46 |
| 16 | 1500 | 3 | 57 |
| 17 | 1500 | 6 | 61 |
| 18 | 1500 | 3 | 19 |
| 19 | 1500 | 20 | 26 |
| 20 | 1500 | 20 | 42 |
| 21 | 1500 | 20 | 16 |
| 22 | 1500 | 3 | 31 |

*The starting reactant of Example 15 was a solution of 29% 3-HP in water
[1]A is ISOPAR K $C_{10}$–$C_{11}$ paraffin, available from Exxon Mobil Company
[2]Ru/C is about 5% ruthenium metal on carbon having about 50% water available from PMC Precious Metals Corporation, Sevierville, Tennessee.

Example 23

The procedures of Examples 1 and 7 are followed except that the carbon support of the ruthenium/carbon catalyst is replaced with a silica support and a zeolite support respectively. It is expected that 1,3-propanediol will be obtained in good yield.

Example 24

The procedure of Example 7 is followed except that the molybdenum oxide is replaced by vanadium oxide and chromium oxide, respectively. It is expected that 1,3-propanediol will be obtained in good yield.

Example 25

The procedures of Examples 1 and 7 are followed except that the Ru/C supported catalyst is replaced by unsupported ruthenium catalyst. It is expected that 1,3-propanediol will be obtained in good yield.

Example 26

The procedures of Examples 1 and 7 are followed except that the Ru/C supported catalyst is replaced by carbon supported ruthenium oxide catalysts. It is expected that 1,3-propanediol will be obtained in good yield.

Example 27

The procedures of Examples 2 and 8 are followed except that the ISOPAR K paraffin liquid phase was replaced by hydrocarbon, alcohol, aromatic compounds such as xylene and ether, respectively. It is expected that 1,3-propanediol will be obtained in good yield.

Example 28

The procedures of Examples 6 and 7 are followed except that the solution of 20% 3-HP in water, is replaced by methyl 3-hydroxypropionate in alcohol, as the starting reactant. It is expected that 1,3-propanediol will be obtained in good yield.

The invention has been described above in detail with particular reference to specific embodiments thereof, but it will be understood that variations and modifications other than as specifically described herein can be effected within the spirit and scope of the invention.

We claim:

1. A process for preparing 1,3-propanediol comprising hydrogenating 3-hydroxypropionic acid in a liquid phase, in the presence of a catalyst comprising ruthenium.

2. The process according to claim 1 wherein the liquid phase is selected from the group consisting of water, organic solvent that is not hydrogenetable, and a mixture of water and to organic solvent.

3. The process according to claim 1 wherein to catalyst comprising ruthenium is selected from the group consisting of ruthenium metal and compounds of nithenium metal.

4. The process according to claim 1 wherein the ruthenium catalyst comprises a supported ruthenium catalyst.

5. The process according to claim 4 wherein the supported ruthenium catalyst comprises ruthenium on a carbon support.

6. The process according to claim 1 wherein the temperature ranges from about 20° C. to about 250° C.

7. The process according to claim 1 wherein the pressure ranges from about 20 p.s.i. to about 4000 p.s.i.

8. A process for preparing 1,3-propariediol comprising hydrogenating 3-hydroxypropionic acid in a liquid phase, in the presence of a catalyst comprising a ruthenium catalyst and at least one or more additional metal catalyst(s).

9. The process according to claim 8 wherein the liquid phase is selected from the group consisting of water, organic solvent tat is not hydrogenatable, and a mixture of water and the organic solvent.

10. The process according to claim 8 wherein to ruthenium catalyst is selected from the group consisting of ruthenium metal and compounds of ruthenium metal.

11. The process according to claim 8 wherein the ruthenium catalyst comprises a supported ruthenium catalyst.

12. The process according to claim 11 wherein the supported ruthenium catalyst comprises ruthenium on a carbon support.

13. The process according to claim 8 wherein the additional metal catalyst comprises a metal or a compound of the metal, wherein the metal is selected from the group consisting of molybdenum, tungsten, titanium, zinonium, niobium, vanadium, chromium, and mixtures thereof.

14. The process according to claim 13 wherein the metal is molybdenum.

15. The process according to claim 8 wherein the additional metal catalyst comprises a supported metal catalyst.

16. The process according to claim 8 wherein the temperature ranges from about 20° C. to about 250° C.

17. The process according to claim 8 wherein the pressure ranges from about 20 p.s.i. to about 4000 p.s.i.

18. A process for preparing 1,3-propanediol comprising hydrogenating a compound selected from the group consisting of 3-hydroxypropionic acid, a C1–C20 alkyl or a C1–C20 aryl ester of 3-hydroxypropionic acid, in a liquid phase, in the presence of a catalyst comprising ruthenium on a carbon support and an additional metal catalyst selected from the group consisting of molybdenum and a molybdenum oxide.

19. The process according to claim 18 wherein the compound is 3-hydroxypropionic acid.

20. The process according to claim 1, wherein the 3-hydroxypropionic acid is produced from a genetically engineered organism.

21. The process according to claim 8, wherein the 3-hydroxyprapionic acid is produced from a genetically engineered organism.

22. The process according to claim 19, wherein the 3-hydroxypropionic acid is produced from a genetically engineered organism.

* * * * *